(12) United States Patent
Ahrend et al.

(10) Patent No.: US 6,443,955 B1
(45) Date of Patent: *Sep. 3, 2002

(54) FRACTURE REDUCTION CLAMP

(75) Inventors: Jon David Michael Ahrend, Sapulpa, OK (US); Don Maddox Womble, Justin, TX (US)

(73) Assignee: Alliance Orthopedic, Inc., Roanoke, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/665,041

(22) Filed: Sep. 19, 2000

Related U.S. Application Data

(63) Continuation of application No. 09/199,598, filed on Nov. 25, 1998.

(51) Int. Cl.[7] .............................................. A61B 17/56
(52) U.S. Cl. .......................... 606/74; 606/103; 606/201
(58) Field of Search ................................ 606/1, 60, 61, 606/74, 86, 102, 103, 201, 203; 81/64, 65, 343; 269/130–132

(56) References Cited

U.S. PATENT DOCUMENTS

| | | |
|---|---|---|
| 1,346,940 A | 7/1920 | Collins |
| 2,049,361 A | 7/1936 | Ericsson |
| 3,111,945 A | 11/1963 | Solbrig |
| 3,507,270 A | 4/1970 | Ferrier |
| 5,116,340 A | 5/1992 | Songer et al. |
| 5,395,374 A | 3/1995 | Miller et al. |
| 5,449,361 A | 9/1995 | Preissman |
| 5,788,697 A | 8/1998 | Kilpela et al. |

FOREIGN PATENT DOCUMENTS

| | | | |
|---|---|---|---|
| DE | 4006696 | 11/1990 | ................... 606/203 |
| GB | 1550186 | 8/1979 | ................... 606/74 |
| SU | 0984467 | 12/1982 | ................... 606/74 |

OTHER PUBLICATIONS

M. E. Muller, M. Allgower, R. Schneider, H. Willenegger, "Manual of Internal Fixation," 1979.
Howmedica 1994 Product Catalog, p. 74.

*Primary Examiner*—Gloria M. Hale
(74) *Attorney, Agent, or Firm*—Randall C. Brown; Haynes and Boone, L.L.P.

(57) ABSTRACT

A fracture reduction clamp for the reduction of a fractured bone. The fracture reduction clamp is particularly suitable for surgical procedures wherein a bone having a fracture is to be fixated with a fixation apparatus after reduction of the bone with a strap. The fracture reduction clamp includes a bifurcated strap guiding head for contacting and firmly gripping the fractured bone, and a strap retainer disposed between the strap guiding head and a rotatable strap tensioner for retaining the ends of the strap being used to reduce the fractured bone. The strap guiding head can include a retractable spike for enhancing the grip of the fractured bone by the fracture reduction clamp. Rotation of the strap tensioner will tighten or loosen the strap about the fractured bone.

20 Claims, 10 Drawing Sheets

FRACTURE REDUCTION CLAMP

This application is a continuation of copending U.S. patent application Ser. No. 09/199,598, filed Nov. 25, 1998, the entire disclosure of which is hereby incorporated herein by reference.

FIELD OF THE INVENTION

The present invention relates generally to a fracture reduction clamp for the temporary reduction or fixation of a fractured bone during a surgical procedure and more specifically, to an improved fracture reduction clamp which provides substantially complete circumferential compression of a fractured bone.

BACKGROUND OF THE INVENTION

Fracture reduction clamps known in the art are used to adjust the tension of a strap or wire surrounding a fractured bone. Known fracture reduction clamps are generally clamp or plier shaped and generally provide only temporary and partial compression of a fractured bone. In use, known fracture reduction clamps generally only provide a two-point compression of a fractured bone and placement of a permanent fixation device onto a fractured bone being reduced generally requires release of the fractured bone by the reduction clamp.

While not clinically used as a fracture reduction clamp, a wire tensioner sold by Howmedica is used to implant a permanent fixation wire about a fractured bone. The bone tensioner of Howmedica comprises a tube-shaped body, a strap guiding head, an adjustable strap retainer and a tension adjustment handle attached to the body and threadably engaged with the strap retainer for adjusting the tension of a strap engaged with the strap retainer and strap guiding head.

The wire tensioner sold by Howmedica generally operates as follows. A strap is passed between a bone having a fracture and the muscle surrounding the bone. The strap is then looped completely around the fractured bone and each end is optionally laced through a crimping sleeve. Each end is then laced through a wheeled end of a strap guiding head and through an adjustable strap retainer. The looping of the wire about the bone provides permanent circumferential compression of the fractured bone when the crimping sleeve is crimped onto the wire. The struts comprising the strap guiding head generally do not grip or resiliently contact the fractured bone. In order to tighten the wire about the bone, a handle on the clamp is rotated thereby displacing the strap retainer further from the fractured bone and tightening the strap surrounding the fractured bone. As the strap tightens about the fractured bone, the bone fragments align and the fracture is reduced. The crimping sleeve is then crimped onto the strap thereby permanently fixating the fractured bone. While the wire tensioner of Howmedica is not used as a fracture reduction clamp, it does share some structural similarity with the presently claimed fracture reduction clamp. However, were the Howmedica wire tensioner to be used in a fashion similar to the present fracture reduction clamp, it could not provide the substantially complete circumferential compression of the fractured bone both before and during placement of a permanent fixation device such as a plate or screw onto or into the fractured bone.

Known fracture reduction clamps generally reduce fractured bones by grasping the bone in a manner resembling pliers. None of the known fracture reduction clamps permit the placement of a bone fixation plate along side a fracture while a strap is tightly surrounding a major portion of the fractured bone, i.e., while maintaining substantially complete circumferential compression of the bone, and none of the known devices comprise a retractable spike in a strap guiding head of the fracture reduction clamp.

SUMMARY OF THE INVENTION

The present invention seeks to address the disadvantages present in fracture reduction clamps known in the art. The fracture reduction clamp can provide substantially complete circumferential compression of a fractured bone while a permanent fixation device is being implanted between the bone and a strap guiding head of the device. The present fracture reduction clamp can provide an orthopedic surgeon the advantages of: reduced overall surgery time; reduced time in which the patient is under anesthesia; reduced blood loss by the patient; reduced stress on the fractured bone and surrounding tissue; and rapid alignment of the fractured bone.

In one aspect, the present invention provides a fracture reduction clamp for tightening a strap about a fractured bone, said clamp comprising:

a substantially hollow tubular body having opposing first and second ends, a coextensive bore therethrough and two slots interposed said first and second ends and intersecting with said bore;

a handle rotatably engaged with said first end of said tubular body;

an externally threaded drive shaft which is fixedly engaged with said handle, disposed within said bore of said tubular body, substantially coaxial with said tubular body, and accessible through said two slots of said body;

a strap retainer which is threadably engaged with said drive shaft, is slidable with respect to said tubular body and extends through said two slots of said tubular body; and a strap guiding head engaged with said second end of said body and comprising opposing, spaced apart, first and second strap guiding struts, each strut having a bore to permit passage of a strap therethrough;

wherein rotation of said handle causes displacement of said strap retainer with respect to said head.

In one embodiment, the fracture reduction clamp can be dismantled by hand into separate components. In another embodiment, the fracture reduction clamp comprises a retractable spike in the head and a thumbwheel to retract and extend the spike. The retractable spike can include a flattened shaft portion which engages a flattened bore portion in the head thereby prohibiting rotation of the spike when the thumbwheel is rotated to displace the spike with respect to the head.

The head of the fracture reduction clamp can include two or more struts having stepped ends for contacting a bone being reduced by the device.

The strap retainer will be adapted to receive and retain a strap that is being used to reduce a bone having a fracture.

The fracture reduction clamp will be adapted to provide substantially complete circumferential compression of a fractured bone, preferably both before and during implantation of a permanent bone fixation device, such as a plate or pin, into or onto the fractured bone, wherein the strap itself is not the permanent fixation device.

The spacing between the first and second strap guiding struts can be made adjustable. In addition, the first and second strap guiding struts can be hingedly mounted onto the strap guiding head.

Another aspect of the invention provides a fracture reduction clamp for tightening a strap about a bone having a fracture, said clamp comprising:

a strap guiding head comprising a spike and at least one strap guide;

a body having a first end engaged with said strap guiding head and a second end;

a rotatable drive engaged with said second end of said body; and a strap retainer adapted to receive and retain a strap passed through said strap guide, said retainer being threadably engaged with said rotatable drive and slidable with respect to said body;

wherein:

said strap retainer is displaced with respect to said strap guiding head when said rotatable driver is rotated.

The strap guiding head can have a bifurcation point at which first and second struts join. The first and second struts can each comprise a strap guide adapted to permit passage of a strap therethrough. The strap guiding head can also comprise a retractable spike which is slidable with respect to said first and second struts. The spike can be made retractable by way of threads on the spike and a thumbwheel threadably engaged with said spike for retracting and extending said spike. The strap guiding head, retractable spike, thumbwheel, tubular body, rotatable drive and strap retainer can each be shaped as desired to optimize performance for a particular use.

Yet another aspect of the invention provides a method of reducing a fractured bone, said method comprising the steps of:

passing a strap around a fractured bone such that said strap surrounds at least a portion of said bone;

passing each of first and second ends of said strap through at least one strap guide in a strap guiding head of a fracture reduction clamp;

engaging each of said first and second ends of said strap with a strap retainer that is slidable with respect to said strap guiding head and is threadably engaged with a rotatable strap tensioner of said fracture reduction clamp; and rotating said strap tensioner such that said strap retainer is displaced away from said strap guiding head thereby tightening said strap about said bone.

The method of the present invention can further comprise the steps of extending or retracting a retractable spike comprised within a strap guiding head used in the method of the invention. Since temporary bone reduction is used in preparation of semi-permanent or permanent bone fixation, the present method of the invention can include steps directed toward fixation of the reduced bone. The bone fixation can be effected with any of a number of available bone fixation apparatuses.

In another embodiment, the invention provides a kit for a fracture reduction clamp, said kit comprising:

at least one tubular body having first and second ends;

at least one strap retainer;

at least two different, removable and interchangeable strap guiding heads which are engageable with said first end of said body; and at least one strap tensioner engageable with said second end of said body and operably engaged with said at least one strap retainer.

The kit of the present invention can independently comprise one or more of each of the individual components of a fracture reduction clamp as described herein. Strap guiding heads of the kit can independently include retractable spikes. The strap guiding heads can differ in dimensions, shape, use, presence or absence of spikes, and in other manners. The strap guiding heads can also include first and second struts having passages for passing a strap therethrough and/or having stepped ends for contacting the surface of a fractured bone being reduced. The individual components of a kit according to the invention can be assembled by hand to form at least one fracture reduction clamp.

Still another embodiment of the invention provides a fracture reduction clamp which together with a strap retained by said clamp is capable of providing substantially complete circumferential compression of a fractured bone before and during implantation of a permanent fixation device into or onto the fractured bone, wherein the strap need not completely encircle the fractured bone.

In this embodiment, the permanent fixation device can be implanted without significantly loosening the strap about the bone. This clamp can also comprise one or more of a spike and a pair of strap guiding struts for contacting the fractured bone during reduction of the fracture. The spike can be fixed or retractable with respect to the clamp. The clamp can also comprise a strap retainer and strap tensioner, and rotation of the strap tensioner can be made to result in tightening of the strap about the fractured bone when the strap is retained by the strap retainer.

Each aspect and embodiment of the invention provides unique and advantageous features which overcome the disadvantages of and which are substantially different than known devices and methods.

Other features, advantages and embodiments of the invention will be apparent to those skilled in the art by the following description, accompanying examples and appended claims.

BRIEF DESCRIPTION OF THE DRAWINGS

The following drawings form part of the present specification and are included to further demonstrate certain aspects of the invention. The invention may be better understood by reference to one or more of these drawings in combination with the detailed description of the specific embodiments presented herein.

FIG. 13a is a bottom plan view of the cap of a strap or retainer according to the invention.

FIG. 13b is a front elevation view of the cap of FIG. 13a.

FIG. 13c is a front elevation view of the body of a sixth embodiment of a strap retainer according to the invention. The body of FIG. 13c is engaged with the caps of FIG. 13b to form a strap retainer.

FIG. 13d is a top plan view of the body of the strap retainer of FIG. 13c.

DETAILED DESCRIPTION OF THE INVENTION

The fracture reduction clamp of the present invention permits a user to apply a torque force to a fractured bone and to place a bone fixation plate alongside a fracture in the fractured bone while a strap of the device is still tightly surrounding the fractured bone and provide either partial or substantially total circumferential compression of a fractured bone. The present fracture reduction clamp is easy to manufacture and can be made with interchangeable heads to permit use of the clamp with various size bones.

Figure 1:
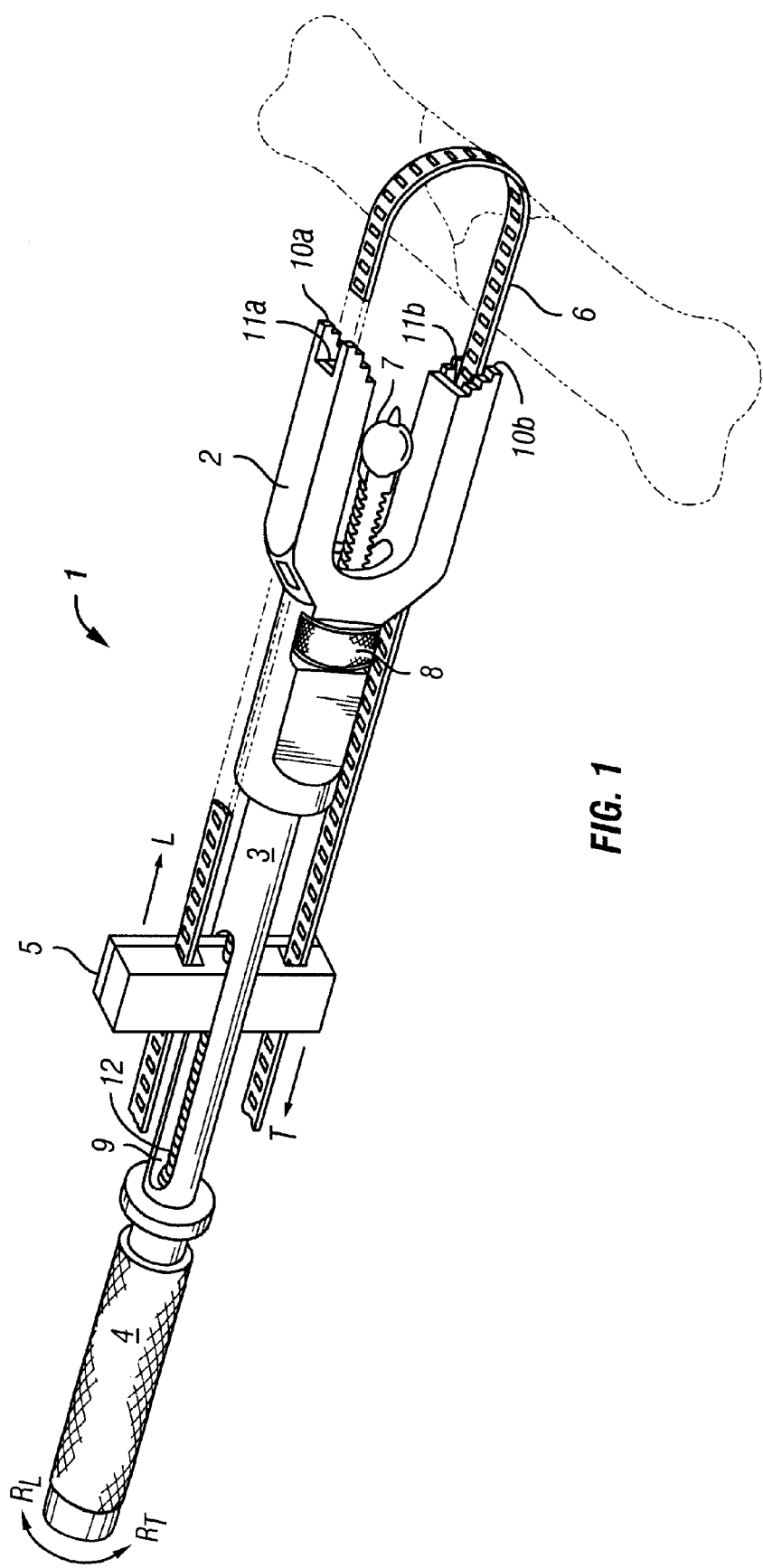
FIG. 1 is a perspective view of a fracture reduction clamp according to the invention.

FIG. 1 depicts a first embodiment of the fracture reduction clamp (1) according to the invention, wherein the clamp (1) comprises a strap guiding head (2), a tubular body (3), a rotatable handle (4), and a strap retainer (5). In the embodiment of FIG. 1, the clamp generally operates as follows. The ends of a strap (6) are passed through bores (11a and 11b) which extend through opposing first and second struts in the strap guiding head (2) mounted on a first end of the tubular body (3). The ends of the strap (6) are then engaged with the strap retainer (5). The handle (4) is rotatably engaged with the tubular body (3) and fixedly engaged with the drive shaft (12). The strap retainer (5) is threadably engaged with the drive shaft (12) and is slidable within the slots (9) of the tubular body (3). As the handle (4) is rotated in the direction of the arrow ($R_T$), the strap retainer (5) is displaced longitudinally along the arrow (T) away from the strap guiding head (2). Since the strap (6) is fixedly engaged with the strap retainer (5), displacement of the strap retainer (5) along the arrow (T) effects a tightening of the strap (6). In a reverse manner, the strap (6) can be loosened by rotating the handle (4) in the direction of the arrow ($R_L$) which effects a forward displacement of the strap retainer (5) in the direction of the arrow (L) toward the strap guiding head (2).

In one embodiment, the fracture reduction clamp (1) includes a strap guiding head (2) that comprises among other things a retractable spike (7) which is operable with a thumbwheel (8). The retractable spike (7) can be extended and retracted during use of the clamp (1). When the spike (7) is brought into contact with a bone (shown in dashed lines) held by the strap (6) and the clamp (1), the spike helps the clamp to grip the bone more firmly.

Figure 2:
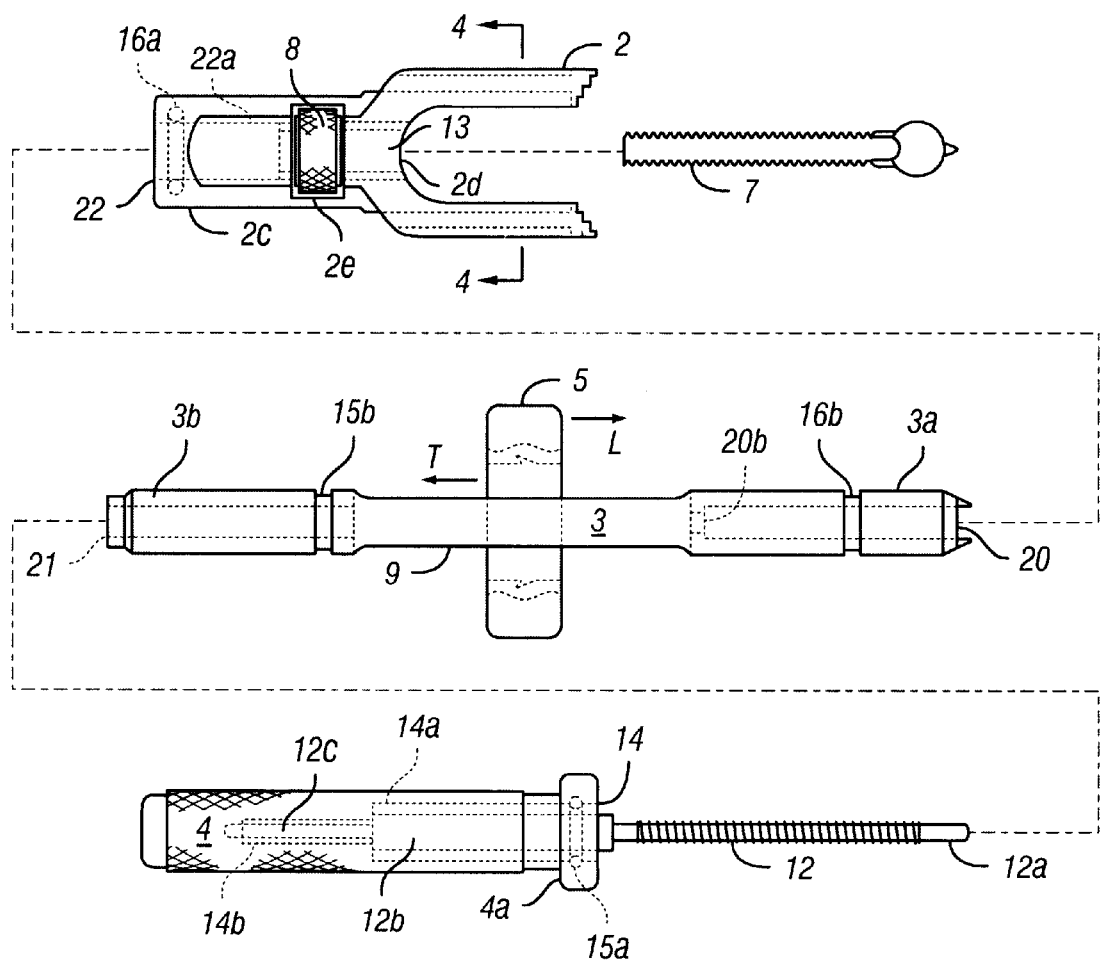
FIG. 2 is an exploded view of the fracture reduction clamp of FIG. 1.

FIG. 2 depicts an exploded view of the fracture reduction clamp (1) of FIG. 1. The tubular body (3) has a first end (3a) which is engageable with the strap guiding head (2) and a second end (3b) which is engageable with the handle (4). The handle (4) comprises a bore (14) which is adapted to receive the second end (3b) of the tubular body (3). In a like fashion, the strap guiding head (2) has a bore (22) which is adapted to receive the first end (3a) of the tubular body (3). The handle (4) and the first end (3b) are held together by a friction joint comprising a retainer ring (not shown), a retainer ring channel (15a) in the handle (4) and a retainer ring channel (15b) in the end (3b) of the tube (3). In a similar fashion, the strap guiding head (2) is engaged with the first end (3) of the tube by way of a compression joint comprising a retainer ring (not shown), a retainer ring channel (16a) in the end (2c) of the head (2) and a retainer ring channel (16b) in the end (3a) of the tube (3).

The handle (4) is fixedly engaged with a drive shaft (12) which comprises a first end (12a), a middle portion (12b) and a second end (12c). The bore (14) of the handle (4) is countersunk and has a wide diameter portion (14a) and a deeper narrow diameter portion (14b). The portion (12c) of the drive shaft (12) is fixedly engaged with the narrow bore (14b) of the handle. The middle portion (12b) of the drive shaft and the inner surface of the bore portion (14a) of the handle define a clearance into which the end (3b) of the tubular body (3) can be placed. The end (3b) has a bore portion (21) which is adapted to receive the drive shaft portion (12b). The outer diameter of the end (3b) is smaller than the inner diameter of the bore (14a) in the handle (4). When the handle (4) is engaged with the end (3b), the end (12a) of the drive shaft (12) will engage a narrow bore (20b) in the tubular body (3), and the end (3b) will occupy the cavity defined by the inner surface of the bore (14a) and the outer surface of the drive shaft portion (12b).

The strap retainer (5) which is slidably engaged with the body (3) is disposed within a slot (9) in the body (3). The slot passes through the body and intersects with a bore which extends throughout the body (3).

When the handle (4) is engaged with the end (3b), the drive shaft passes through the bore (21) and threadably engages the strap retainer (5). Ultimately, the end (12a) of the drive shaft (12) will engage the narrow bore (20b) which serves as a guide or bearing for the end (12a).

The strap guiding head (2) has a countersunk bore (22) therethrough from a first end (2c) to a point of bifurcation (2d). The countersunk bore has a narrower diameter bore portion (13) which is adapted to receive the shaft of a retractable spike (7). The head (2) has a slot (2e) therethrough which intersects with the bore portion (13) and which is adapted to receive a thumbwheel (8). When the spike (7) and the end (3a) are engaged with their respective bore portions (13 and 22) of the head (2), the shaft of the spike (7) will pass through the bore portion (13) and into the bore (20) located at the first end (3a) of the tubular body (3).

Figure 3:
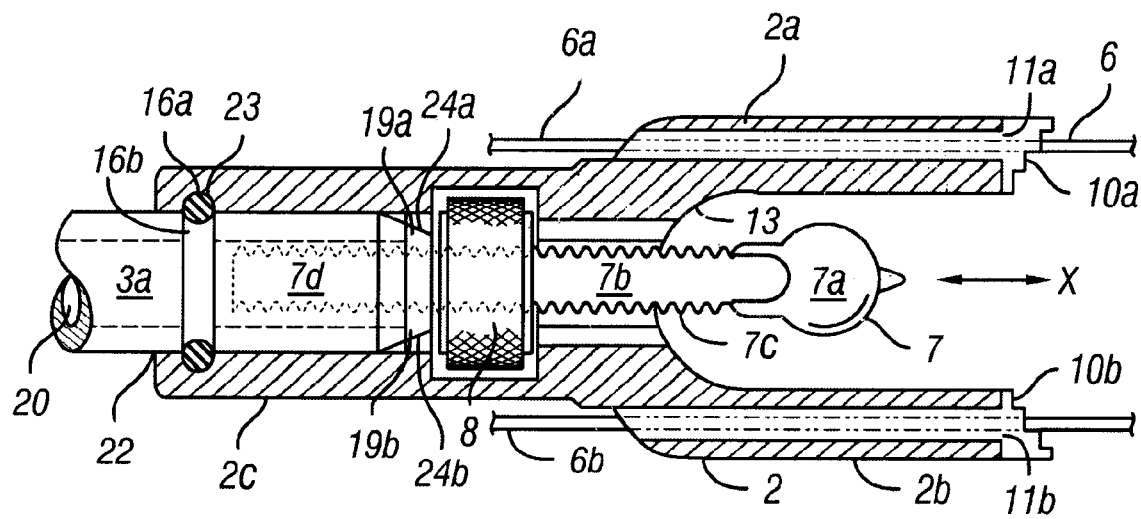
FIG. 3 is a cross-sectional view of the strap guiding head (2) according to the invention.

Referring now to FIG. 3, the strap guiding head (2) comprises a first strut (2a) and a second strut (2b), the first strut (2a) having a bore (11a) therethrough and the second strut (2b) having a bore (11b) therethrough. The bores (11a and 11b) are adapted to receive respective portions (6a and 6b) of a strap (6) when the fracture reduction clamp is in use. The spike depicted in FIG. 3 has a head portion (7a), a shaft portion (7b) and an opposing end (7d). The shaft portion (7b) will have a flattened surface portion which extends substantially coaxially with the linear axis of the spike (7). The spike (7) will also have an externally threaded portion (7c) which also extends substantially coaxially with the linear axis of the spike (7). The thumbwheel (8) is shown as being threadably engaged with the threaded portion (7c) of the spike (7).

The end (3a) of the body (3) has a male coupling comprising a pair of projections (19a and 19b) which engage with a female coupling comprising a pair of recesses (24a and 24b) disposed within the inner bore (22) of the head (2). The male coupling of the end (3a) and the female coupling of the head (2) serve to prohibit rotation of the tubular body (3) within the bore (20) of the head (2) so that when the handle (4) is rotated, the body (3) will not rotate with respect to the head (2). When the end (3a) and the spike (7) are engaged with the head (2), the end (70) of the spike will pass through the bore (13) and into the bore (22). The outer surface of the shaft portion of the spike and the inner surface of the bore (22) of the head will define a clearance within which the end (3a) of the tubular body (3) is placed.

By rotation of the thumbwheel in either a counterclockwise or clockwise direction, the spike (7) can be made to retract and extend longitudinally along the axis of the bore (13) in the direction of the arrow (X).

Figure 4:
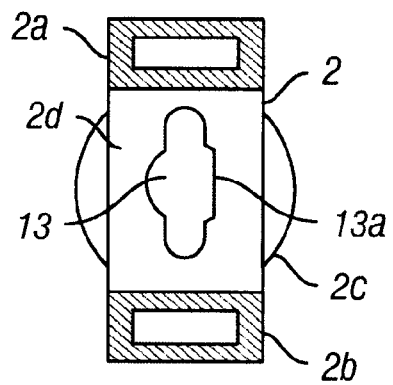
FIG. 4 is a cross-sectional view along lines 4—4 of the strap guiding means (2) in FIG. 2.

FIG. 4 depicts a cross-sectional end view of the head (2) along lines 4—4 of FIG. 2. The bore (13) located at the bifurcation point (2d) of the head (2) comprises a flattened portion (13a) which engages the flattened portion (7b) of the shaft of the spike (7). The engagement of the flattened portion (13a) and flattened portion (7b) assures that the shaft of the spike (7) will not rotate within the bore (13) when the thumbwheel (8) is rotated, thereby making it possible for the thumbwheel (8) to drive the spike in a reciprocal manner within the bore (13). The flattened portion (13a) can be considered exemplary of a stopping means adapted to stop rotation of the spike shaft when it is engaged with a rotatable thumbwheel (8). Other means for stopping the rotation of a shaft can be used in place of the flattened portion (13a). Such means can include a slot and pin combination, a channel and pin combinations, a key and notch combination wherein the key is on the shaft and the notch is in the strap guiding head and others known to those of ordinary skill in the art.

Referring again to FIG. 3, the bores (11a and 11b) extend substantially the entire length of the struts (2a and 2b), respectively. However, it is only necessary that the bores (11a and 11b) extend a sufficient length of their respective struts (2a and 2b) to permit passage of strap portions (6a and 6b) through the bores (11a and 11b).

The ends (10a and 10b) of the struts (2a and 2b), respectively, are depicted as having stepped ends that are declined toward each other and toward the bifurcation point (2d). However, the ends (10a and 10b) can be smooth, stepped, serrated, roughened, knurled, inclined, declined or otherwise formed. In a preferred embodiment, the ends (10a and 10b) will enhance the gripping of a fractured bone by the fracture reduction clamp so that the clamp can be used to apply a torque to a bone being reduced by the clamp.

Figure 16:
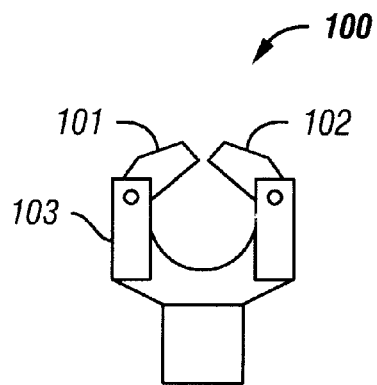
FIG. 16 is a side elevation view of another embodiment of the strap guiding head of the invention having hingedly or pivotally mounted struts.
Figure 17:
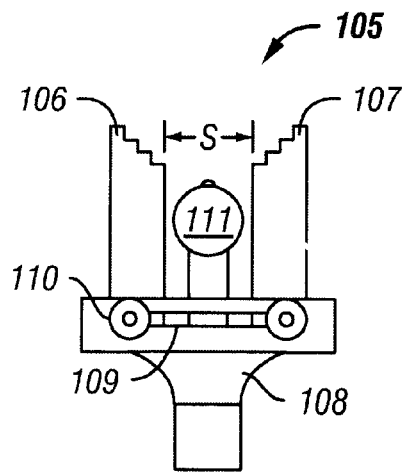
FIG. 17 is a side elevation view of another embodiment of the strap guiding head of the invention wherein the spacing between the struts is adjustable.
Figure 18:
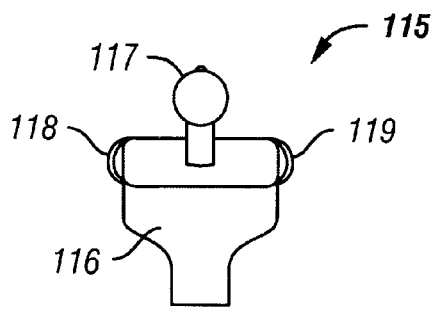
FIG. 18 is a perspective view of another embodiment of the strap guiding head of the invention wherein the head has no struts but includes a spike.

Various alternate embodiments of the strap guiding head according to the invention are shown in FIGS. 16–18. FIG. 16 depicts a first embodiment wherein the strap guiding head (100) comprises first (101) and second (102) struts which are hingedly or pivotally mounted onto the body (103). In order to provide a firm grasp of a reduced bone, the strap guiding head (100) can also comprise a locking means (not shown) which is used, when needed, to secure the relative positions of the struts. FIG. 17 depicts a second embodiment wherein the strap guiding head (105) comprises first (106) and second (107) struts adjustably mounted onto the body (108) by way of adjustment means comprising the slot (109) and locking screws (110). The spacing (S) between the struts (106, 107) is made adjustable with adjustment means. The strap guiding heads (100, 105) can be used to fit a variety of different bone sizes. In other alternate embodiments, a strap guiding head can include hingedly mounted first and second struts which are also adjustable such that a space therebetween can be adjusted.

FIG. 18 depicts a third embodiment of the strap guiding head (115) wherein the head has no struts but does include a spike (117) which is fixed or retractable engaged with the body (116). The strap guiding head (116) comprises strap guides (118, 119) which are adapted to permit passage of a strap therethrough. As used herein, the term "strap guide" can be, for example, a loop, tube, channel, passageway, or hook.

The strap retainer (5) according to the invention will be threadably engaged to a drive shaft (12) or other drive means, will be slidable with respect to the tubular body (3) and will be displaceable away from or toward the strap guiding head (2) in response to rotation of the drive shaft (12). The retainer (5) will not rotate with respect to the tubular body (3).

Figure 5:
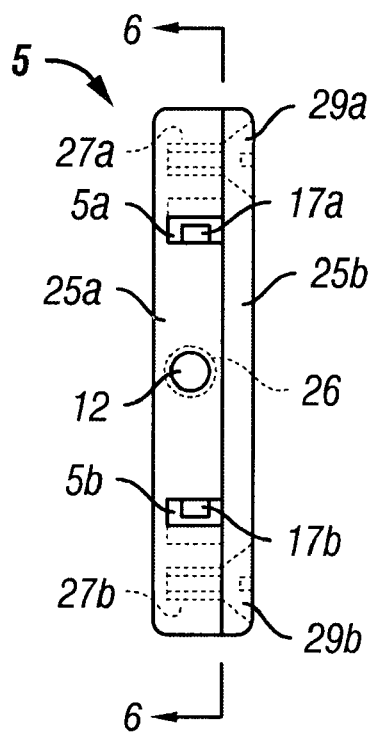
FIG. 5 is a front elevation view of a strap retainer according to the invention.

The strap retainer according to the invention will retain a strap in either a reversible or irreversible fashion. In the embodiment of FIG. 5, the strap retainer (5) comprises at least one retaining member (17a), a passageway (5a) adapted to receive a strap, a body (25a) and an internally threaded bore (26) which is adapted to threadably engage a drive shaft (12).

In the embodiment of FIG. 5, the strap retainer (5) comprises a body portion (25a) and a cover portion (25b) which are secured to each other by way of attachment means. The attachment means can comprise any known means for securing two solids to each other. By way of example and without limitation, the attachment means in the embodiment of FIG. 5 includes at least one screw (29a) and at least one threaded bore (27a) in the body portion (25a). Attachment means can include clamps, adhesive, welds, screws, rivets, nails, brackets, straps, pins and other such means known to those of skill in the art.

The body portion (25a) comprises a threaded bore (26) therethrough which is threadably engageable with a drive shaft (12). The body portion (25a) also includes a passageway such as, by way of example and without limitation, an aperture, bore, channel, space, clearance, cavity or crevice which is adapted to receive a strap.

The body portion (25a) also includes at least one retaining member (17a) which is disposed either within or adjacent the passageway (5a) and which is adapted to retain a strap inserted through the bore (5a) at least momentarily. The retaining member (17a) will engage a strap either reversibly or irreversibly depending on the particular construction of the retaining member (17a) and of the strap used. In a preferred embodiment, the strap retainer (5) will comprise two bores (5a, 5b) therethrough which are adapted to receive a strap and two retaining members (17a and 17b) disposed in the respective bores (5a and 5b) which are adapted to retain respective first and second ends of a strap.

Figure 6:
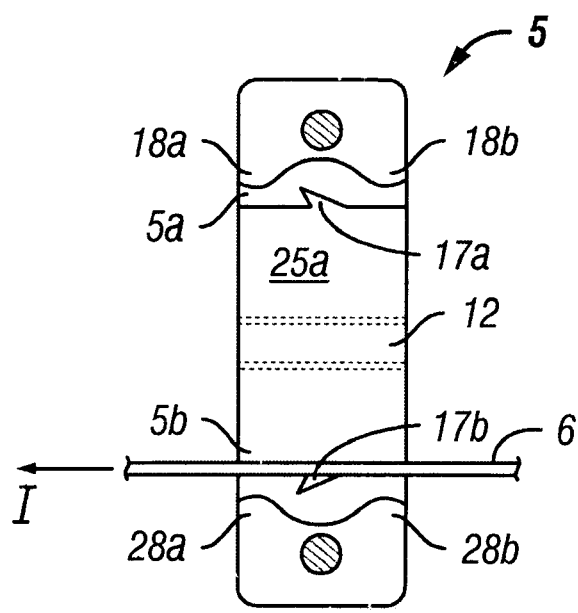
FIG. 6 is a top plan view along lines 6—6 of the retainer (5) of FIG. 5.

Referring now to FIG. 6, the body portion (25a) of the strap retainer (5) of FIG. 1 is depicted as having two passageways (5a and 5b) for receiving respective first and second ends of a strap. When the passageways (5a and 5b) are covered with the cover portion (25b), the passageways together with the respective portions of the cover (25b) form bores through the strap retainer (5). In order to assist in maintaining a strap (6) engaged with a respective strap retaining member (17b), the strap retainer (5) can further comprise strap biasing means (28a, 28b) which bias a strap (6) disposed within the passageway (5b) toward the retaining member (17b).

Figure 7:
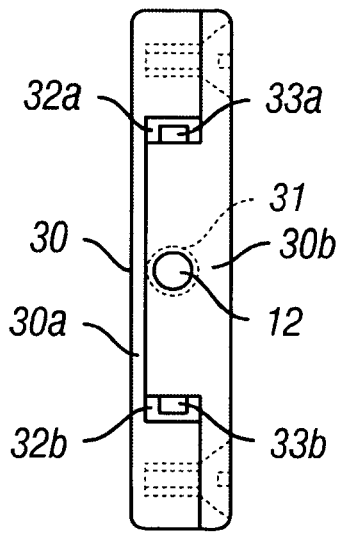
FIG. 7 is a front elevation view of a second embodiment of the strap retainer according to the invention.

FIG. 7 depicts another embodiment of the strap retainer (30) according to the invention comprising a first body portion (30a) and a second body portion (30b) wherein the body portions are held together by attachment means. In this embodiment, the body portion (30a) comprises a strap biasing means (not shown), and the body portion (30b) comprises a threaded bore (31) and two retaining members (33a and 33b). When assembled to form the strap retainer (30), the body portions (30a and 30b) together define two passageways (32a and 32b) which are adapted to receive first and second ends of a strap (not shown). The retaining members (33a and 33b) will be disposed within the passageways (32a and 32b), respectively.

Figure 8:
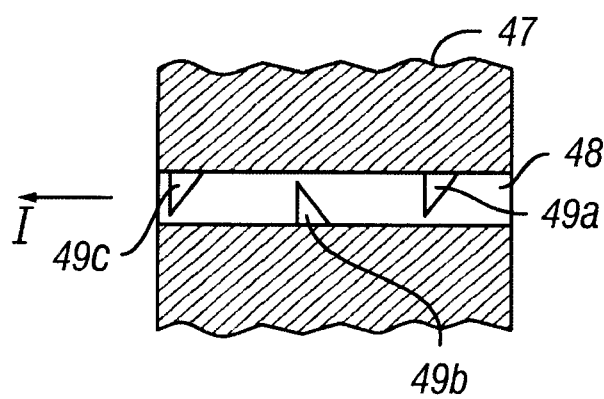
FIG. 8 is a partial sectional view of a third embodiment of the passageway of the strap retainer according to the invention.

FIG. 8 depicts a partial cross-sectional view of a strap retainer (47) which comprises a passageway (48) which is adapted to receive a strap (not shown) inserted therethrough in the direction of the arrow (I). The strap retainer (47) will irreversibly retain a strap, i.e., once inserted through the passageway (48) in the direction of the arrow (I), a strap will not be able to be withdrawn in a direction opposite of the arrow (I). The irreversible retention of the strap is made possible by the use of a strap having slots or apertures which irreversibly engage one or more of the retaining members (49a, 49b and 49c) disposed within the passageway (48). The strap retainer (47) need not comprise strap biasing means as placement of the retaining members (49a and 49c) in a direction opposite that of the retaining member (49b) assures a secure engagement of the retaining members with the strap.

Figure 9:
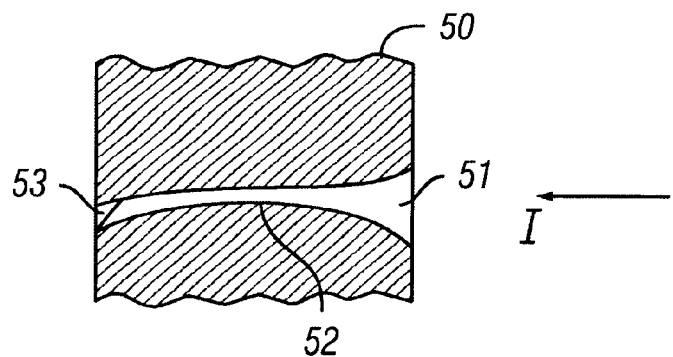
FIG. 9 is a partial sectional view of a fourth embodiment of the passageway of the strap retainer according to the invention.

FIG. 9 depicts a partial cross-sectional view of yet another embodiment of the strap retainer (50) according to the invention wherein the strap retainer comprises an arcuate passageway (51) and a retaining member (53) disposed therein. In this embodiment, the curved wall (52) serves as a strap biasing means as described above.

FIGS. 13a–d depict various elevation and plan views of another embodiment of the strap retainer (60) according to the invention. The strap retainer comprises a body (61), two opposing end caps (62a) and (62b) mounted on opposing ends (61a) and (61b), respectively, of the body (61), a threaded bore (73) which can be threadably engaged with a threaded drive shaft (12), a first retaining member (66a) and a second retaining member (66b). The end caps (62a) and (62b) depicted in FIG. 13b comprise cover portions (70a) and (70b), respectively, convex arcuate surfaces (68a) and (66b), respectively, adjacent the end cap, retaining members (66a) and (66b), respectively, adjacent the convex arcuate surfaces (68a) and (68b), respectively, and end portions (64a) and (64b), respectively. When the end cap (70a) is engaged with the end portion (61a) of the body (61), the end portion (64a) of the end cap (62a) abuts the end portion (63a) of the body (61). The cover portion (70a), the channel (67a) and the body (61) together define a passageway through which a strap can be passed and retained by the strap retainer (61). The channel (67a) is defined by an arcuate convex surface (65a) and an opposing biasing surface comprising a first (69a) and a second (71a) biasing means. The biasing surface biases a strap disposed within the channel (67a) toward the arcuate surface (65a), the arcuate surface (68a) of the end cap (62a) and the retaining member (66a) of the end cap (62a). When the strap is inserted in the channel (67a), notches or slots within the strap will engage the retaining member (66a) preferably in an irreversible manner.

Figure 13:
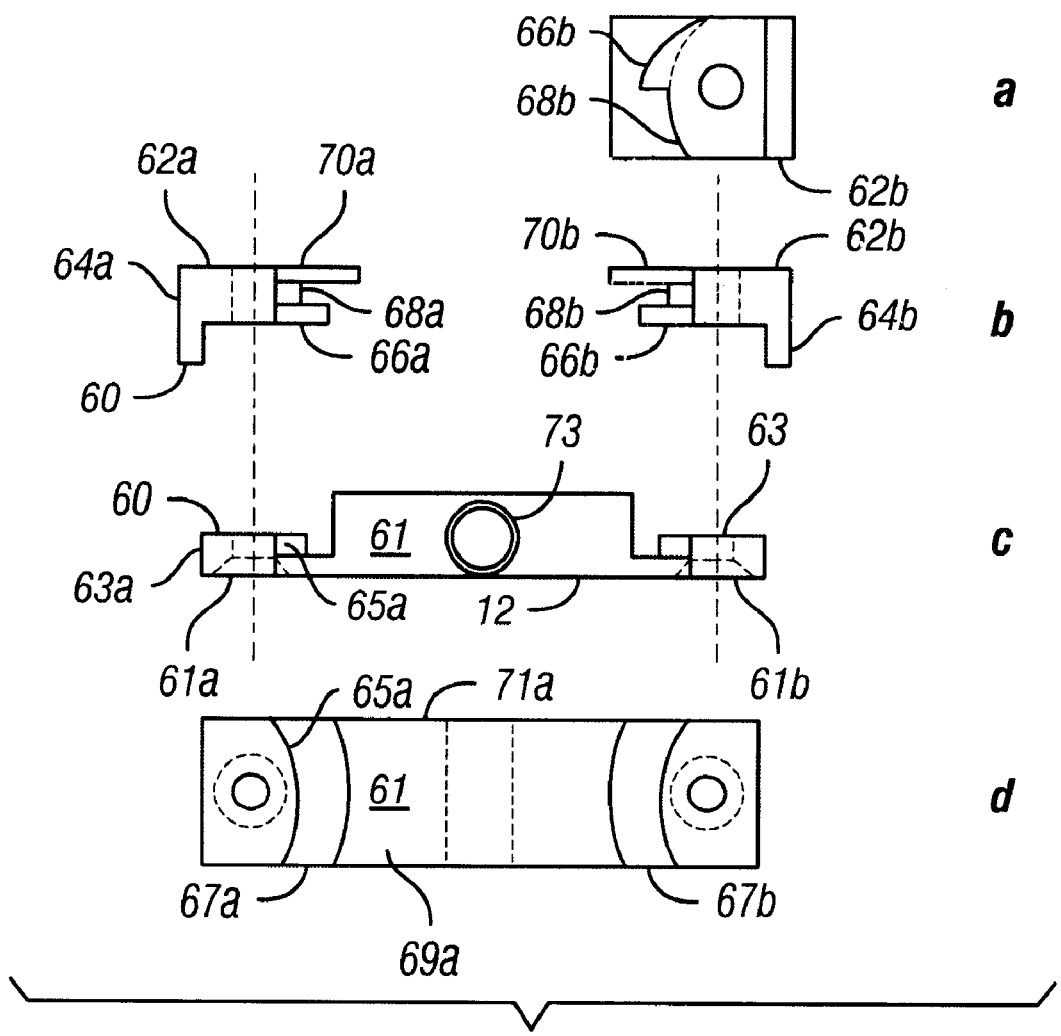

The end caps (62a) and (62b) are attached to the respective end portions (63a) and (63b) of the body (61) by way of attachment means which can comprise any means used to affix, attach, or engage two solids together. In the embodiment of FIG. 13b and 13c, the strap retainer (61) comprises a countersunk bore (63b) in the first end (61b) of the body (61) and a threaded bore (70b) in the end cap (62b). The end cap and the body can be held together by a threaded screw that is engaged with both the end cap and the body.

In the embodiment of FIGS. 13a–d, the strap retainer (61) comprises two retaining members (66a, 66b), two biasing means, a body portion (61), two end caps (62a, 62b), two channels (67a, 67b), and a threaded bore (73) in the body portion (61).

Figure 10:
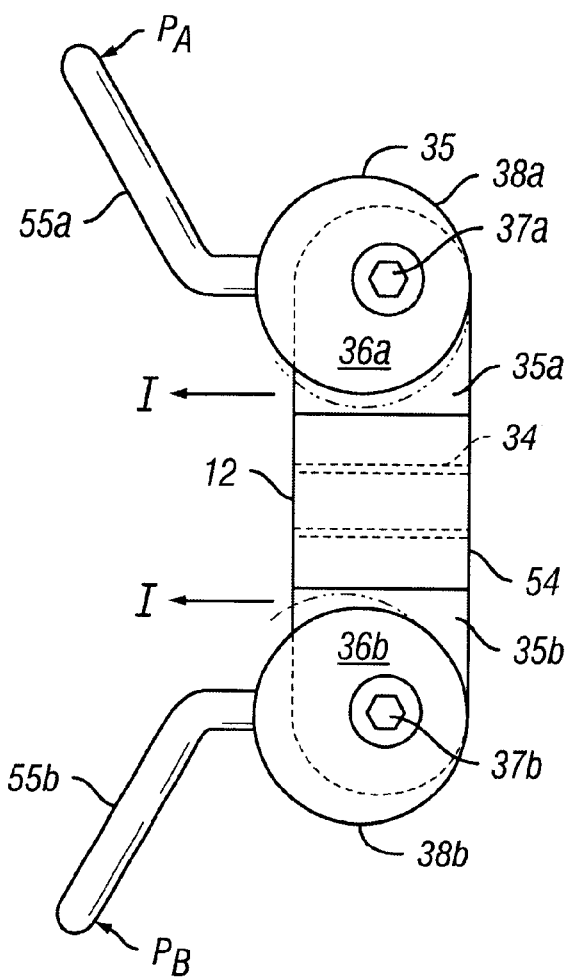
FIG. 10 is a top plan view of a fifth embodiment of the strap retainer according to the invention.

It is not necessary that the strap retainer engage a strap irreversibly. The strap retainer (35) depicted in FIG. 10 permits reversible engagement of a strap (not shown). The strap retainer (35) comprises a body portion (54), a threaded passageway (34) which is threadably engageable with a threaded drive shaft (12) or rotatable driving means, a first thumbwheel (36a) and a second thumbwheel (36b). Each thumbwheel has a respective outer periphery (38a and 38b) which, together with adjacent portions of the body (54), define clearances (35a and 35b), respectively, which are adapted to receive first and second ends of a strap. The wheels (36a and 36b) are mounted eccentrically onto the body (54) by way of wheel retainers (37a and 37b) about which the respective wheels (36a and 36b) pivot. When the handle (55a), which is attached to the wheel (36a), is swung in the direction of the arrow ($P_A$), the outer periphery (38a) is brought closer to an opposing portion of the body (54) thereby narrowing the clearance of the passageway (35a) When a strap is inserted in the passageway (35a) in the direction of the arrow (I) and the outer periphery (38a) is in resilient or firm contact with the strap, the strap will temporarily not be able to be retracted from the clearance (35a) in a direction opposite to that of the arrow (I). A strap being retained by the strap retainer (35) can be released simply by swinging the handle (55a) away from the strap in a direction opposite that of the arrow ($P_A$), thereby making engagement of a strap by the retainer (35) reversible.

Figure 11:
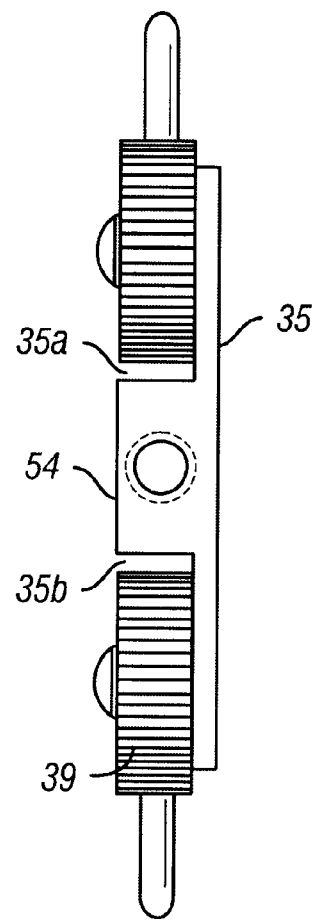
FIG. 11 is a front elevation view of the strap retainer of FIG. 10.

Referring now to FIG. 11, the wheels (36a and 36b) of the strap retainer (35) can have textured (39) outer peripheries to facilitate gripping of a strap being retained by the strap retainer (35). The texture (39) can be hash marks, knurling, surface roughening, and other such textures that increase the frictional resistance between the surface of a strap and the surface on the outer periphery of the respective wheels. It will be understood that the textured surface can occur on the surface of the retainer that defines the passageway rather than on the outer periphery of the wheels.

Figure 12A:
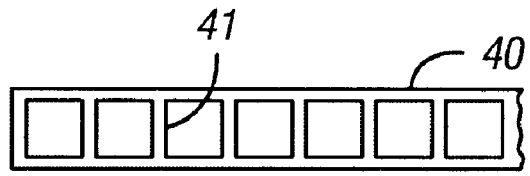
FIGS. 12a–12c are top plan views of various alternate embodiments of the strap used with the fracture reduction clamp according to the invention.
Figure 12B:
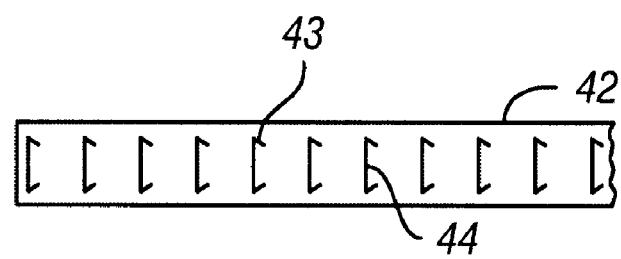
Figure 12C:
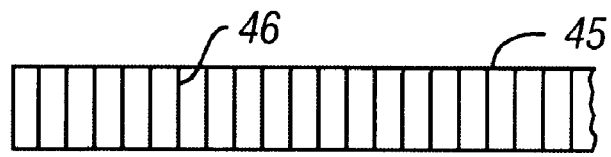

The strap retainer according to the invention can be adapted to engage and retain a wide variety of straps. FIGS. 12a, 12b and 12c depict three alternate embodiments of straps that can be used. FIG. 12a depicts a strap (40) having plural apertures or slots (41) which apertures engage with at least one retaining member in a strap retainer according to the invention. FIG. 12b depicts a strap (42) having plural incisions (43) which form plural flap portions (44) in the strap when it is engaged with a retaining member. The flap (44) will be displaced from its first position to a second position thereby permitting a retaining member to engage with an aperture formed by the incision (43). FIG. 12c depicts a strap (45) having a textured surface (46) which increases the friction between the strap (45) and a retaining member. The texture on the surface (46) can include by way of example and without limitation hash marks, knurlings, irregular surface markings, and other such friction-enhancing means known to those of skill in the art.

As used herein, the term "strap" is taken to mean a strip of material, a cord, a string, a wire, a barlock, a cable, a twine, a fiber, a band, a nylon cord, fishing string, a strand, and other such materials that can be used in the art of bone reduction and fixation. A strap according to the invention will be flexible and dimensioned to permit retention by a strap retainer according to the invention. A strap for use in the present clamp can be obtained from the Tyton Corporation (Milwaukee, Wis.).

The fracture reduction clamp according to the invention need not be, but is preferably, adapted to being dismantled and assembled by hand. A fracture reduction clamp can be provided as a unit having a strap guiding head permanently affixed to an end of a tubular body or removably engaged with an end of a tubular body. The tubular body can be adapted to removably and interchangeably engage with at least two different strap guiding heads.

When the fracture reduction clamp according to the invention is provided as a kit, the kit will comprise at least one tubular body having first and second ends, at least one strap retainer, at least two different removable and interchangeable strap guiding heads which are engageable with the first end of the tubular body, and at least one strap tensioner engageable with the second end of the body and operably engageable with the at least one strap retainer.

It will be preferred that at least one of the strap guiding heads present in the kit will have a retractable spike and even more preferable that the strap guiding head further include a thumbwheel for retracting and extending the retractable spike. Generally, the strap guiding heads will have first and second struts wherein each strut has a bore which is adapted to permit passage of a strap therethrough. The at least two different, removable and interchangeable strap guiding heads can differ in size, dimension, shape, use, materials of construction, purpose of use, and/or design.

The at least one retainer in the kit according to the invention can be adapted to either reversibly or irreversibly retain a strap and can comprise fixed, movable, or rotatable retaining members which engage the strap. When the components of a kit according to the invention are assembled to form a fracture reduction clamp, the strap retainer will preferably be slidable with respect to the body and displaceable from the strap guiding head. Even more preferred, the strap retainer will be threadably engaged with the strap tensioner, and the strap retainer will slide with respect to the tubular body when the strap tensioner is rotated.

Although a wide variety of constructions for the retractable spike can be used in the present invention, a preferred retractable spike will have a first head portion, a shaft portion, a longitudinally extending threaded portion and a longitudinally extending unthreaded and flattened portion. Even more preferably, the retractable spike will retract and extend from a point of bifurcation in the strap guiding head in response to rotation of a thumbwheel in the strap guiding head.

The fracture reduction clamp according to the present invention is useful for a variety of methods of reducing a fractured bone. One such general method comprises the following steps:

passing a strap around a fractured bone such that the strap is disposed between the outer surface of the bone and overlying muscle tissue;

passing first and second ends of the strap through strap guides in a strap guiding head of a fracture reduction clamp;

engaging the first and second ends of the strap with a strap retainer that is displaceable away from and slidable with respect to the strap guiding head and is threadably engaged with a rotatable strap tensioner included in the clamp; and rotating the strap tensioner such that the strap retainer is displaced away from the strap guiding head thereby tightening the strap about the fractured bone and at least temporarily reducing the fracture.

In one embodiment, the method of the invention can further comprise the step of extending a retractable spike comprised within a strap guiding head, wherein this particular step can be conducted either before or after any one of the other steps in the method of the invention. The method can also comprise the step of retracting the retractable spike after the step of rotating the strap tensioner.

The method according to the invention can further comprise the step of placing a bone fixation apparatus between the strap guiding head and the fractured bone wherein the step can be conducted before or after any one of the other steps of the invention. The bone fixation apparatus can also be placed between the retractable spike and the fractured bone. Either after partial or complete reduction of a fractured bone by the fracture reduction clamp according to the invention, the method of the invention allows for fixation of the fractured bone with a bone fixation apparatus.

Figure 14:
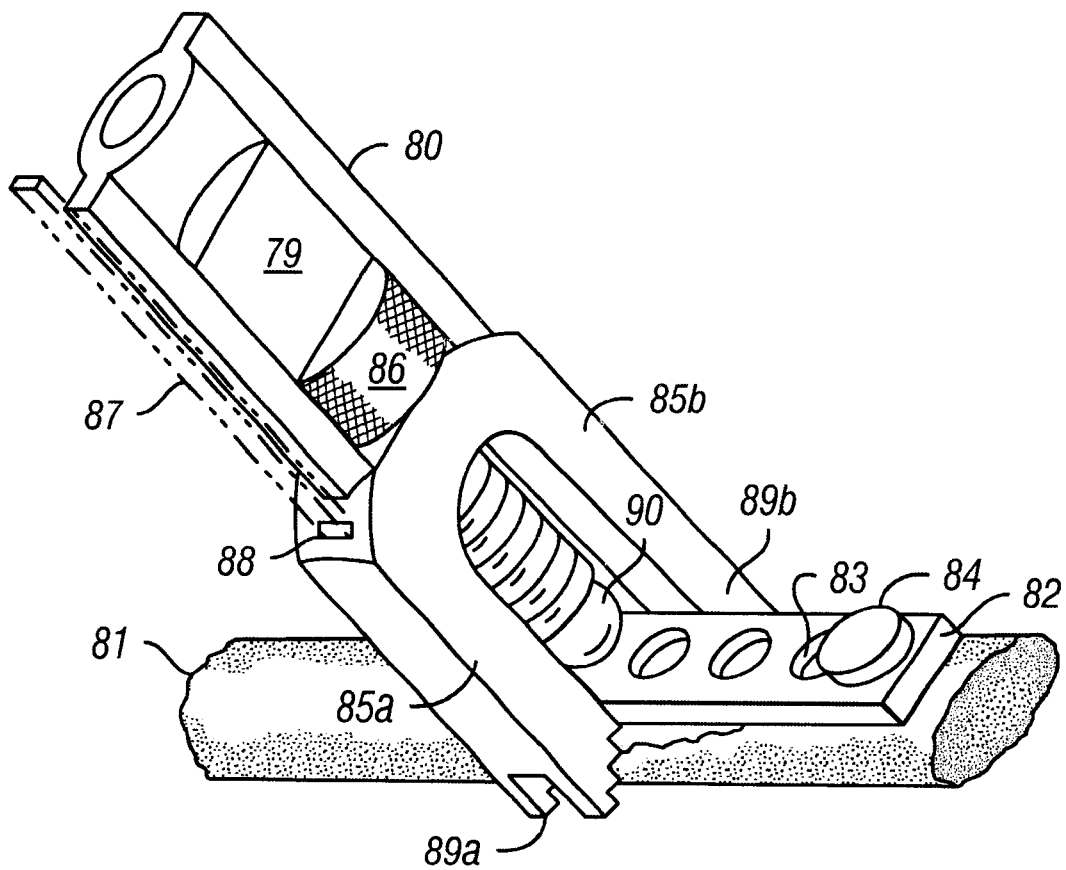
FIG. 14 is a perspective view of a fracture reduction clamp according to the invention reducing a fractured bone.

One embodiment of the method of the invention is shown in FIG. 14 which depicts a reduction clamp (80) being used to reduce an obligue fracture in the bone (81). The clamp (80) comprises a strap guiding head (79) which comprises first (85a) and second (85b) struts, a retractable spike (90), a thumbwheel (86) used to retract the spike (90), and a bore (88) through the struts (85a, 85b) through which a strap (87) passes. The fixation plate (82) is shown affixed to the bone (81) by way of a fixation screw (84) which passes through a hole (83) in the plate.

The method of the invention, as depicted in FIG. 14, was conducted as follows. The strap (87) was passed around the bone (81) between the bone and surrounding muscle tissue (not shown). The ends of the strap (87) were passed through the bore (88) in each of the first (85a) and second (85b) struts and subsequently engaged with a strap retainer (not shown) of the clamp (80). The strap (87) was then tightened about the bone until the ends (89a, 89b) of the struts (85a, 85b) abutted the bone (81). The spike (90) was then extended until it contacted the bone (81). This step can be done before several of the previous and following steps. As the strap (87) was further tightened, the fracture was reduced by the clamp (80). The struts (85a, 85b) in combination with the strap (87) and the spike (90) provided a substantially complete circumferential compression of and a firm grasp of the bone (81). The spike (90) was then retracted, by way of the thumbwheel (86), a sufficient amount to permit insertion of the fixation plate (82) over the oblique fracture in the bone (81) without any significant loss in circumferential compression. The head of the spike (90) was then extended again and engaged with a hole (83) in the plate (82). The plate (82) was then affixed to the bone (81) with a screw (84). Following completion of bone fixation with the plate (82) and other screws (84), the strap (87) was loosened and then removed.

It should be noted that the grasp of a bone by the clamp of the invention is sufficiently firm that the expected range of motion of the fractured bone, once it has healed, can be predicted simply by reduction of the fractured bone and articulation of the bone. This method can be practiced without having to permanently fixate the fractured bone with a fixation device. An exemplary embodiment of the method of predicting the range of motion of a fractured bone, once the bone has healed, includes the steps of: reducing a fractured bone with a fracture reduction clamp according to the invention; and articulating the fractured bone that has been reduced to determine its range of motion; wherein the range of motion of the fractured bone that has been reduced approximates the range of motion that can be achieved for the bone once its fracture has healed.

Figure 15A:
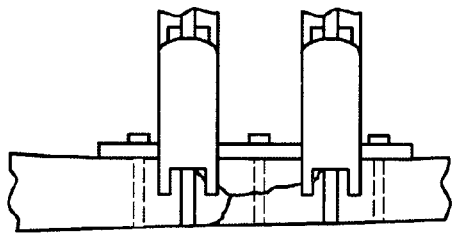
FIGS. 15a–15d are side elevation views of the fraction reduction clamp reducing a variety of different types of fractures.
Figure 15B:
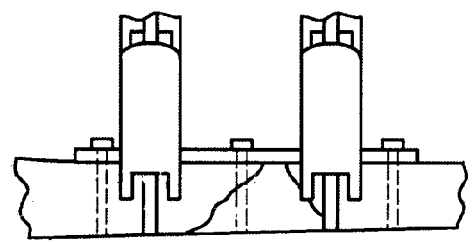
Figure 15C:
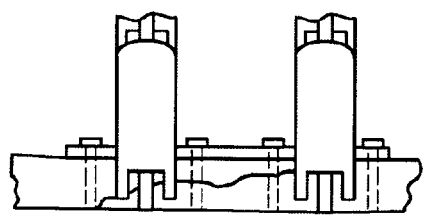
Figure 15D:
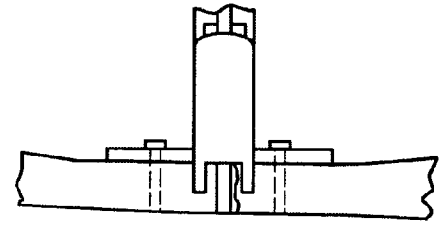

FIGS. 15a–15d depict several different types of fractures that can be reduced with the present fracture reduction clamp. Such fractures include simple, compound and comminuted fractures such as, for example, butterfly fractures (FIG. 15a), spiral fractures (FIG. 15b), long oblique fractures (FIG. 15c) and transverse fractures (FIG. 15d). As depicted in these figures, it may necessary to employ more than one fracture reduction clamp (only shown in part) in reducing a fractured bone. Accordingly, the method of the invention can include additional steps directed toward reducing a fractured bone with one or more clamps according to the invention.

As used herein, a bone fixation apparatus can comprise a screw, nail, wire, plate, bracket, rod, pin, adhesive, clamp, or other such apparatuses known to those of skill in the art.

It will be understood by those of ordinary skill in the art that the materials of construction for the fracture reduction clamp of the present invention can comprise any known materials typically used for this purpose. For example, various metals, stainless steel, alloys, plastics, and/or polymers.

The fracture reduction clamp depicted in the attached figures can be used by either a right-handed or left-handed person; however, the bone reduction apparatus can be adapted for preferred use by just a right-handed or just a left-handed user.

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

What is claimed is:

1. A fracture reduction clamp for tightening a strap about a fractured bone, said clamp comprising:

a substantially hollow tubular body having opposing first and second ends, a coextensive bore therethrough and two slots interposed said first and second ends and intersecting with said bore;

a handle rotatably engaged with said first end of said body;

an externally threaded drive shaft which is fixedly engaged with said handle, disposed within said bore of said body, substantially coaxial with said body, and accessible through said two slots of said body;

a strap retainer which is threadably engaged with said drive shaft, is slidable with respect to said body and extends through said two slots of said body; and a strap guiding head engaged with said second end of said body and comprising a spike and at least one strap guide which permits passage of a strap therethrough;

wherein rotation of said handle causes displacement of said strap retainer with respect to said head.

2. The bone reduction clamp of claim 1 wherein said spike is retractable.

3. The fracture reduction clamp of claim 2 wherein said head further comprises a thumbwheel for retracting and extending said spike.

4. The fracture reduction clamp of claim 1 wherein said strap retainer has at least one passageway adapted to receive and retain a strap.

5. The fracture reduction clamp of claim 4 wherein said strap retainer includes at least retaining member for retaining a strap.

6. The fracture reduction clamp of claim 1 wherein said bore of said body comprises at least two portions having different diameters.

7. The fracture reduction clamp of claim 1 wherein said clamp can be dismantled by hand into separate components.

8. The fracture reduction clamp of claim 1 wherein said head is removably engaged with said second end of said body.

9. The fracture reduction clamp of claim 1 wherein said spike comprises a threaded first portion and an opposing, substantially flat and unthreaded second portion.

10. The fracture reduction clamp of claim 9 wherein said strap guiding head comprises a bore having a substantially flat portion which engages said substantially flat and unthreaded second portion of said spike thereby to prevent said spike from rotating when said thumbwheel is rotated to retract or extend said spike.

11. The fracture reduction clamp of claim 2, wherein said spike is retractable into said strap guiding head.

12. A fracture reduction clamp for tightening a strap about a fractured bone, said clamp comprising:

a substantially hollow tubular body having opposing first and second ends, a coextensive bore therethrough and two slots interposed said first and second ends and intersecting with said bore;

a handle rotatably engaged with said first end of said body;

an externally threaded drive shaft which is fixedly engaged with said handle, disposed within said bore of said body, substantially coaxial with said body, and accessible through said two slots of said body; p1 a strap retainer which is threadably engaged with said drive shaft, is slidable with respect to said body and extends through said two slots of said body; and p1 a strap guiding head engaged with said second end of said body and comprising opposing, first and second strap guiding struts that are adjustable to create a space there between, each strut having a bore to permit passage of a strap therethrough; p1 wherein rotation of said handle causes displacement of said strap retainer with respect to said head.

13. The fracture reduction clamp of claim 12 wherein said strap retainer has at least one passageway adapted to receive and retain a strap.

14. The fracture reduction clamp of claim 13 wherein said strap retainer includes at least retaining member for retaining a strap.

15. The fracture reduction clamp of claim 12 wherein said bore of said body comprises at least two portions having different diameters.

16. The fracture reduction clamp of claim 12 wherein said clamp can be dismantled by hand into separate components.

17. The fracture reduction clamp of claim 12 wherein said head is removably engaged with said second end of said body.

18. The fracture reduction clamp of claim 12 wherein each of said first and second strap guiding struts has stepped ends for contacting a fractured bone being reduced by said clamp.

19. The fracture reduction clamp of claim 18 wherein said stepped ends are declined toward each other.

20. The fracture reduction clamp of claim 18, wherein said first and second strap guiding struts are hingedly engaged with said strap guiding head.

* * * * *